(12) United States Patent
Narasimhan et al.

(10) Patent No.: US 11,623,017 B1
(45) Date of Patent: Apr. 11, 2023

(54) SMART AIR-PURIFICATION SYSTEM

(71) Applicants: Narayanan Narasimhan, Plano, TX (US); Venkateswaran H, Chennai (IN)

(72) Inventors: Narayanan Narasimhan, Plano, TX (US); Venkateswaran H, Chennai (IN)

( * ) Notice: Subject to any disclaimer, the term of this patent is extended or adjusted under 35 U.S.C. 154(b) by 0 days.

(21) Appl. No.: 17/734,271

(22) Filed: May 2, 2022

(51) Int. Cl.
*A61L 9/20* (2006.01)
*A61L 9/22* (2006.01)

(52) U.S. Cl.
CPC ............... *A61L 9/20* (2013.01); *A61L 9/22* (2013.01); *A61L 2209/111* (2013.01); *A61L 2209/14* (2013.01)

(58) Field of Classification Search
CPC ......... A61L 9/20; A61L 2209/111; A61L 9/22
See application file for complete search history.

(56) References Cited

U.S. PATENT DOCUMENTS

| | | | |
|---|---|---|---|
| 2005/0186108 A1* | 8/2005 | Fields | A61L 2/202 422/123 |
| 2021/0308311 A1* | 10/2021 | Stewart | F24F 8/22 |
| 2022/0010996 A1* | 1/2022 | Carrieri | F24F 11/39 |

* cited by examiner

*Primary Examiner* — Kevin Joyner

(57) ABSTRACT

A smart air-purifier system to provide improved air quality in a negative pressure enclosure is disclosed. The system comprises a machine housing that encloses a filter unit to remove airborne particles. The filter unit includes a high-efficiency particulate air (HEPA) filter. The system further includes one or more sensors to monitor the air quality and maintain the random forest approach (RAQ) for predicting air quality, a server to store a plurality of real-time data of the air-purifier system, and a user device to access the plurality of data stored in the server. Further, the real-time data is analyzed using internet-of-things (IoT) to perform surveillance to capture and monitor infection prevention and control data using a mobile application. The system further comprises a four-node controller inside the machine housing configured to switch on and off the system. Also, the system further comprises one or more ultraviolet (UV) lamps and an ionizer.

11 Claims, 14 Drawing Sheets

SMART AIR-PURIFICATION SYSTEM

FIELD OF THE INVENTION

The present invention generally relates to the field of air purification systems. More specifically, the present invention relates to a smart air purification system to create a best sterile environment in enclosed spaces in a short time.

BACKGROUND

The airborne disease is caused by microorganisms that are transmitted through the air. Many airborne diseases include bacteria, viruses, and fungi. These airborne diseases can spread when an infected person cough, sneeze, and sprays into the air resulting in the airborne transmission of microorganism in the person who breaths in. Airborne diseases are more prominent than ever and COVID-19 has taken a lot of lives. Some of the airborne diseases include chickenpox, measles, mumps, influenza, whooping cough, tuberculosis, covid-19, and more.

For example, Tuberculosis (TB) is transmitted from person to person through the air by a person with TB disease of the lungs. Similarly, the less frequency aerobic bacterium is transmitted by ingestion of *Mycobacterium bovis* found in unpasteurized milk products, laboratory accidents. Also, measles is highly contagious and spreads through the air when an infected person coughs and sneezes. It is so contagious that if one person has it, 9 out of 10 people of all ages around him or her will also become infected, if they are not protected.

Further, harmful emissions have resulted in poor air quality. Breathing poor air or polluted air for long periods of time increases the risk of respiratory infections and can affect the heart and cardiovascular system. For example, cities like Delhi have the worst air quality and their indoor air quality is even worse. At the same time, indoor air pollution is the chemical, biological, and physical contamination of air quality inside the home which severely impacts the quality of people's health. This indoor air pollution could be up to 10× times more than the outer air pollution. The indoor air pollution is due to the emission of chemical fumes (volatile organic compound—VOC). The VOC includes pet dander, mites, virus, bacteria, and outdoor air pollution. The outdoor pollution concentrates because of low air circulation. These VOC are emitted from printers, combustion gas, cleaning products, air fresheners, carpet, floor cleaners, and more. The indoor air pollution can result in burning eyes, digestive problems, memory problems, sinus problems, breathlessness, dizziness, muscle, and joint pain, sleep issues, cough, fatigue, nausea, sore throat, chronic running nose, headache, poor concentration, and more. The most affected people groups are women and young children, as they spent maximum time at home. Moreover. 76% of the homes and houses had unhealthy air quality of over 250 microns per cubic meter.

Indoor air pollution is the $2^{nd}$ highest killer after high blood pressure. This kills around 1.3 million people every year in India. The average indoor pollution level in India is 375 ug/m3, the world health organization (WHO) prescribes a limit of up to 20 ug/mg. the common indoor air pollutants are airborne particles from diesel, exhaust, dust, smoke, and other sources; indoor formaldehyde from building materials, furniture, cooking, and smoking; household odors and gases from activities such as painting, cooking, and smoking; Ozone from outdoor air (ground-level ozone is harmful to breathe); and carbon dioxide from people exhaling and cooking.

There exist various systems and methods for monitoring air purification. Few existing patent references attempted to address the problems cited in the background as prior art over the presently disclosed subject matter and are explained as follows:

A prior art US 20200256578A1 assigned to Michael A. Meis et. al., entitled "Air filter condition sensing" discloses devices, systems, and methods for obtaining data associated with air filter media of an air filter, and for using such data to generate an air filter recommendation, such as an indication of the air filter media condition to a user, an indication that the filter needs replacing, and/or a recommendation to use a different type of filter.

Another prior art US 20220010996 A1 assigned to John carrieri, entitled "Cloud based HVAC management apparatus and system for air purification, indoor air quality monitoring, and methods for implementing the same" discloses a uniquely designed air-purification, remote HVAC management, and indoor air quality monitoring system including an online cloud-based platform. In various embodiments, the air purification system is configured for generating a photocatalytic oxidation reaction so as to purify the air traversing through an HVAC unit. The system may be a locally based system that utilizes a specially designed Artificial Intelligence platform for optimizing energy efficiency, enthalpy, and air quality based on continual sensor data collection, indoor air quality measurements, and dynamically adjusted operating parameters. A fault indicator and communications display may also be included.

Another prior art U.S. Pat. No. 11,137,163 B2 assigned to Vasileios nasis, entitled "Environment monitoring and management systems and methods" discloses a method for managing air quality may include, at one or more processors, receiving sensor data comprising a plurality of air quality parameters for an environment, wherein the sensor data is generated by one or more environment quality monitoring devices located in the environment, predicting an adverse air quality event based on the sensor data, and automatically controlling one or more devices to mitigate the adverse air quality event. An environment quality monitoring device may include a housing, a plurality of sensors in the housing and configured to generate sensor data comprising a plurality of environment quality parameters, a network communication device configured to communicate the sensor data over a network, and an alert configured to indicate an environment quality score of the ambient environment, where the environment quality score is based on at least a portion of the sensor data.

Another prior art WO 2019091987 A1 assigned to Jing Su, et. al., entitled "Smart air purification" discloses an air purification monitoring system for monitoring an air purification apparatus adapted to purify air in an enclosed space. The air purification monitoring system comprises a processor arranged to receive an indication of a spontaneous ventilation rate between the enclosed space and the outdoor space; determine the spontaneous ventilation rate from said received indication; and generate a control signal for an air flow displacement arrangement of the air purification apparatus as a function of said calculated spontaneous ventilation rate, said control signal causing the air flow displacement arrangement to control a rate of a forced ventilation airflow such that the forced ventilation airflow rate exceeds the spontaneous ventilation rate. Also disclosed are an air purification apparatus, a method and computer program product.

Though the above prior art discloses various systems and methods for monitoring air purification but none of them disclosed a smart air-purification system that purifies the air in a negative pressure enclosure along with the real-time data for analysis. Further, a system for monitoring and maintaining the air quality by evaluating the real-time data in a short time is nowhere disclosed.

Further, in the existing systems, the non-availability of portable solutions results in higher infrastructure investments and time consumption. Also, the non-availability of relevant data is a cause of concern for the experts to analyze and evaluate the problem i.e., no real-time data for analysis.

Therefore, there is a need for a smart air purification system that provides a one-stop solution for better air and improved quality of breathing in a negative pressure enclosure. Further, there is a need for a system that creates the best sterile environment in a short time at affordable costs. Also, there is a need for a system that monitors and maintains the air quality by evaluating the real-time data in a short time. And also, there is a need for a system that provides the best contamination control and infection prevention in a negative pressure enclosure.

SUMMARY OF THE INVENTION

The present invention generally discloses an air purification system. Also, the present invention discloses a smart air purification system that provides a one-stop solution for better air and improved quality of breathing in a negative pressure enclosure. Further, the present invention discloses a smart air purification system to create a best sterile environment in enclosed spaces in a short time at affordable cost.

According to the present invention, a smart air-purifier system for improving air quality is disclosed. In one embodiment, the system is an artificial intelligence (AI) based smart air purification system for providing contamination control and infection prevention in a negative pressure enclosure (NPE) conforming to Centers for Disease Control and Prevention (CDC) & World Health Organization (WHO) norms. Further, the system monitors and maintains the air quality by evaluating the real-time data. In one embodiment, the system provides a portable quick clean air solution in a short time. in one embodiment, the system is used in negative pressure enclosure or environment at ER and post-operative ICU to provide quick clean air solutions. In one embodiment, further the system also protects other people in the room, outside of the NPE.

In one embodiment, the air-purifier system comprises an air-purifier machine housing that encloses an air filter unit. The air filter unit is used for removing airborne particles from the air. In one embodiment, the machine housing includes a four-node controller configured to switch on and off the system. In one embodiment, the system further includes a smoke sensor coupled to the machine to detect and switch off the system when there is any sort of smoke. In one embodiment, the system further includes UV lamps, ionizers, and other devices that are enclosed inside the machine housing.

In one embodiment, the system further includes one or more sensors fixed away from the machine in a sensor box. In one embodiment, the sensors include a set of PM 2.5 (particulate matter 2.5), $CO_2$ sensors, humidity sensor, temperature sensor, and other sensors. In one embodiment, the sensors are configured to monitor the air quality and maintain the random forest approach for predicting air quality (RAQ). In one embodiment, the RAQ is maintained at an average of 25 micrograms per cubic meter by switching on the machine when the level reaches an optimum level i.e., 40 µg/cu·m. In one embodiment, the machine is switched off till it gets down to 10 micrograms per cubic meter. So, on a daily average, it will be around 25 µg/cu·m mean value.

In one embodiment, the system further includes a server (i.e., Microsoft Azure) in communication with the machine via a communication network configured to store a plurality of real-time data of the air-purifier system. In one embodiment, the system further includes a user device associated with the user. In one embodiment, the user device communications with the server via the communication network configured to access the plurality of data that are stored in the server. In one embodiment, the data is analyzed using internet-of-things (IoT) to perform surveillance to capture and monitor infection prevention and control data. In one embodiment, the user device includes a user interface configured to analyze the real-time data. In one embodiment, the user device is installed with a dedicated application software or mobile application or web-based application, or desktop application software for analyzing real-time data. In one embodiment, the dedicated application software has a dashboard and one or more air purifier controls. In one embodiment, the user device enables the user to access one or more services provided by the system. In one embodiment, the user device is at least any one of a smartphone, a mobile phone, a tablet, a laptop, a desktop, and/or other suitable hand-held electronic communication devices.

In one embodiment, the machine housing comprises a front housing and a back housing. In one embodiment, the back housing further includes one or more holes for receiving the air tubes. In one embodiment, the machine housing further includes a filter fixed next to the front housing. In one embodiment, the filter is used to circulate the air and capture particles and gases. In one embodiment, the machine housing further includes a front frame attached with the front housing and a back frame attached with the back housing. In one embodiment, the machine housing further includes a plurality of fastening holes for receiving fasteners. In one embodiment, the back frame further includes an attachment with a slot for receiving a high-efficiency particulate air (HEPA) filter. In one embodiment, the machine housing further includes an ON and OFF switch and a button.

In one embodiment, further the real-time data from the air purifier is analyzed using IoT to perform surveillance to capture and monitor infection prevention and control data. In one embodiment, the real-time data includes energy consumption, life of the filter, filter replacement alert, room air quality parameters of PM 2.5 and $CO_2$ level. In one embodiment, all the data are uploaded in real-time and are available for download to a system in excel format for further analysis. In one embodiment, the system complies with mandates of the National Accreditation Board for Hospitals & Healthcare Providers (NABH) Clause HIC.6. In one embodiment, the data is displayed in the user device. In one embodiment, the real-time data is accessible through a user device or mobile application via the server. In one embodiment, the user device displays the air-purifier control data in a dashboard to the customer for analysis anywhere using IoT.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific methods and structures disclosed herein. The description of a method step or a structure referenced by a numeral in a drawing is applicable to the description of that method step or structure shown by that same numeral in any subsequent drawing herein.

DETAILED DESCRIPTION OF EMBODIMENTS

Figure 1:
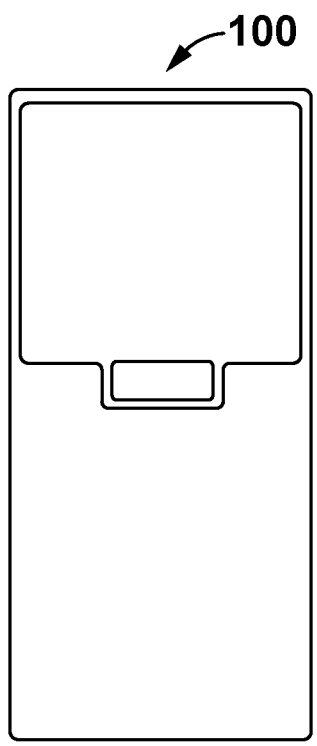
FIG. 1 shows a front view of a smart air-purifier system for improving air quality in an embodiment of the present invention.
Figure 2:
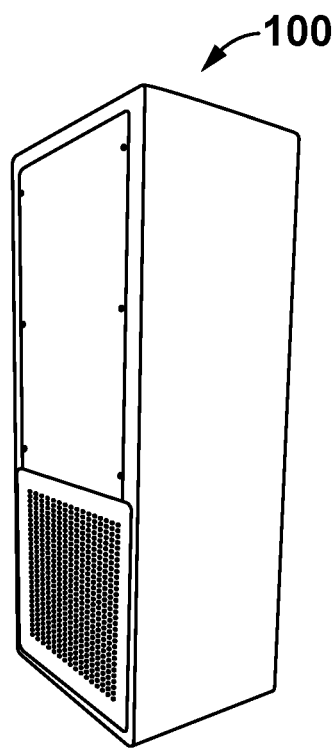
FIG. 2 shows a side perspective view of the smart air-purifier system in an embodiment of the present invention.
Figure 3:
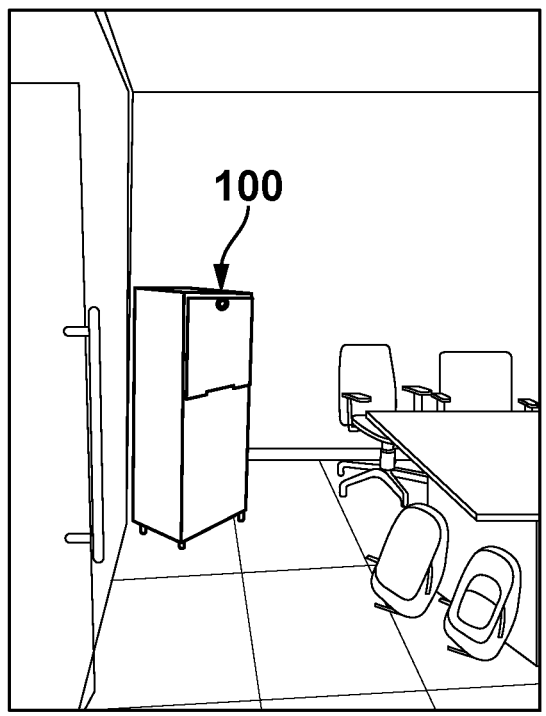
FIGS. 3-4 show the smart air-purifier installed in a workspace in a typical use case in one embodiment of the present invention.
Figure 4:
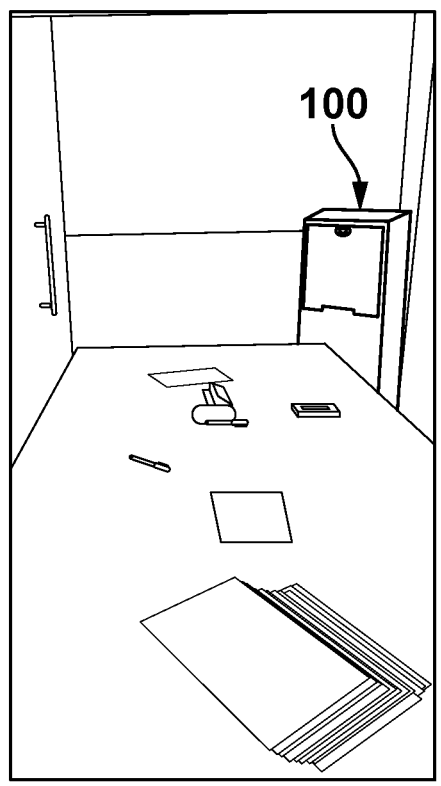

The present invention is best understood by reference to the detailed figures and description set forth herein.

It is expected that the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

Referring to FIGS. 1-4, a smart air-purifier system (hereinafter referred as system) 100 for improving air quality, according to one embodiment of the present invention. In one embodiment, the system 100 is an artificial intelligence (AI) based smart air purification system for providing contamination control and infection prevention in a negative pressure enclosure (NPE) conforming to Centers for Disease Control and Prevention (CDC) & World Health Organization (WHO) norms. Further, the system 100 monitors and maintains the air quality by evaluating the real-time data. In one embodiment, the system 100 provides a portable quick clean air solution in a short time. in one embodiment, the system 100 is used in negative pressure enclosure or environment at ER and post-operative ICU to provide quick clean air solutions. In one embodiment, the system 100 further protects other people in the room, outside of the NPE (i.e., from the airborne infectious agents carried by the person inside the NPE).

In one embodiment, the air-purifier system 100 comprises an air-purifier machine housing that encloses an air filter unit. The air filter unit is used for removing airborne particles from the air. In one embodiment, the machine housing includes a four-node controller configured to switch on and off the system 100. In one embodiment, the system 100 used in various locations is shown (in FIGS. 3 and 4). In one embodiment, the system 100 is the only portable solution complying with CDC Norms of >12 ACPH in 1600 CFT area in class 100 condition. Further, the system 100 complies to WHO norms of 25 µg/cu·m as day average. In one embodiment, the system 100 further includes a smoke sensor coupled to the machine to detect and switch off the system 100 when there is any sort of smoke. In one embodiment, the system 100 further includes UV lamps, ionizers, and other devices that are enclosed inside the machine housing.

In one embodiment, the system 100 further includes one or more sensors fixed away from the machine in a sensor box. In one embodiment, the sensors include a set of PM 2.5 (particulate matter 2.5), $CO_2$ sensors, humidity sensor, temperature sensor, and other sensors. In one embodiment, the sensors are configured to monitor the air quality and maintain the random forest approach for predicting air quality (RAQ). In one embodiment, the RAQ is maintained at an average of 25 micrograms per cubic meter by switching on the machine when the level reaches an optimum level i.e., 40 µg/cu·m. In one embodiment, the machine is switched off till it gets down to 10 micrograms per cubic meter. So, on a daily average, it will be around 25 µg/cu·m mean value.

In one embodiment, the system 100 further includes a server (i.e., Microsoft Azure) in communication with the machine via a communication network configured to store a plurality of real-time data of the air-purifier system. In one embodiment, the system 100 further includes a user device associated with the user. In one embodiment, the user device communications with the server via the communication network configured to access the plurality of data that are stored in the server. In one embodiment, the data is analyzed using internet-of-things (IoT) to perform surveillance to capture and monitor infection prevention and control data. In one embodiment, the user device includes a user interface configured to analyze the real-time data. In one embodiment, the user device is installed with a dedicated application software or mobile application or web-based application, or desktop application software for analyzing real-time data. in one embodiment, the dedicated application software has a dashboard and one or more air purifier controls. In one embodiment, the user device enables the user to access one or more services provided by the system. In one embodiment, the user device is at least any one of a smartphone, a mobile phone, a tablet, a laptop, a desktop, and/or other suitable hand-held electronic communication devices.

Figure 5:
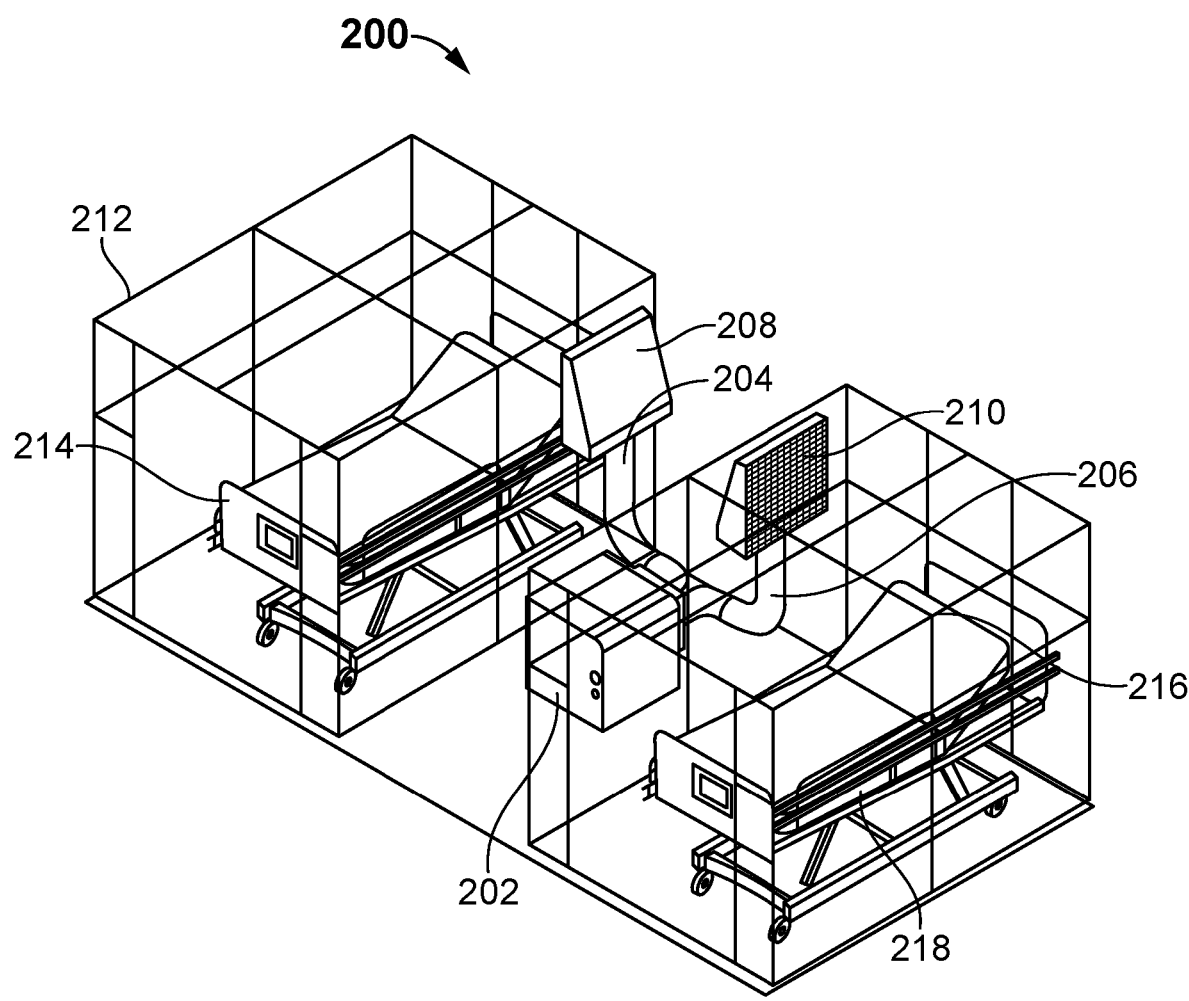
FIG. 5 shows a smart air-purifier installed in a negative pressure enclosure to handle more than one cabin in one embodiment of the present invention.

Referring to FIG. 5, a smart air-purifying system 200 installed in a negative pressure enclosure to handle more than one cabin, according to one embodiment of the present invention. In one embodiment, the system 200 comprises a machine housing 202 that encloses an air purifier unit and one or more internal components. The machine housing 202 is connected to one or more air purifier via one or more air tubes to clean more than one cabin at a time. In one embodiment, the machine housing 202 is connected to at least two air-purifiers (208 and 210) via the air tubes (204 and 206) respectively, for cleaning two cabins (212 and 216) at a time. In one embodiment, each cabin (212 and 216) includes one or more cabin beds (214 and 218) for facilitating users. In one embodiment, the system 200 cleans the air in the cabins (212 and 216), thereby providing clean air and preventing infection at a same time in a negative pressure enclosure or the enclosed space in a short time.

Figure 6:
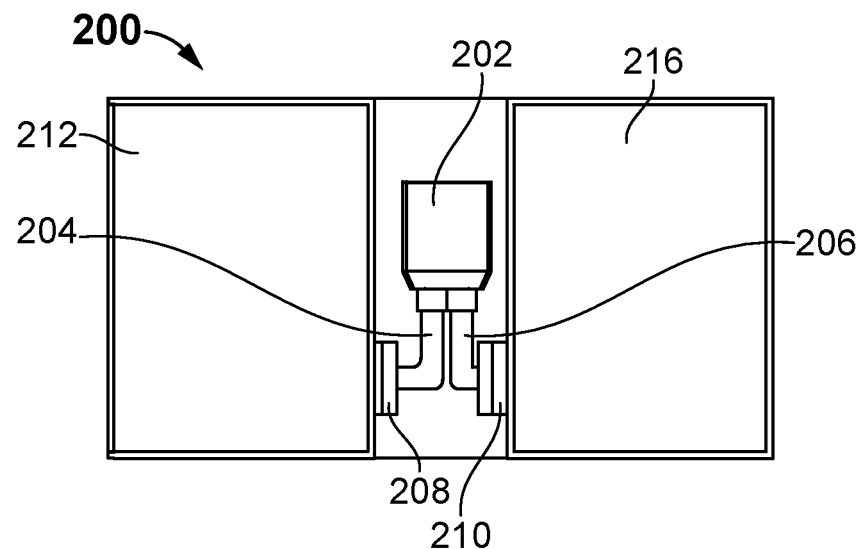
FIGS. 6-9 show various views of the smart air-purifier installed in the negative pressure enclosure in one embodiment of the present invention.
Figure 7:
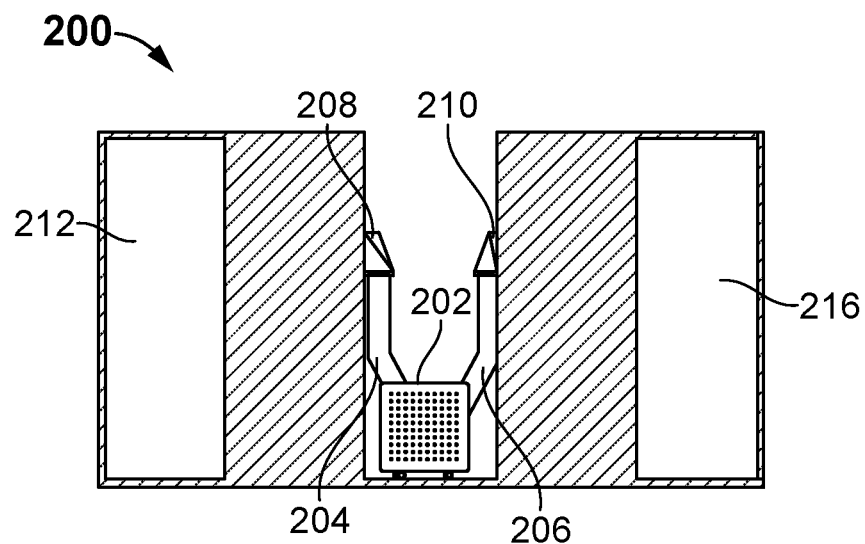
Figure 8:
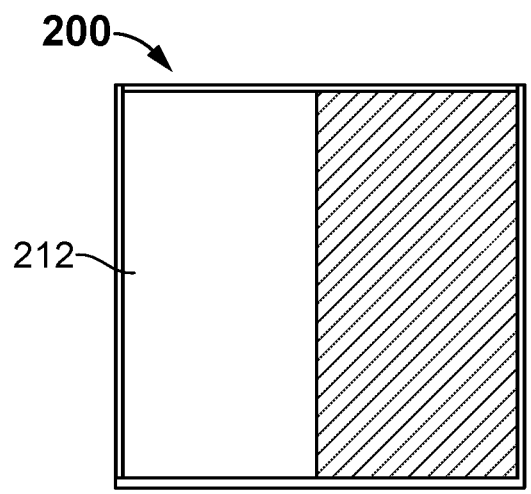
Figure 9:
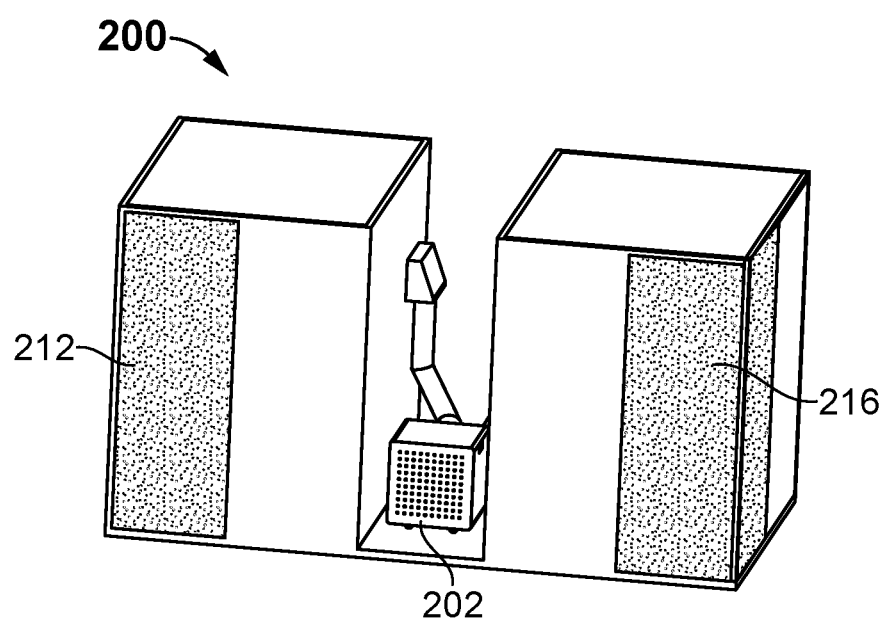
Figure 10:
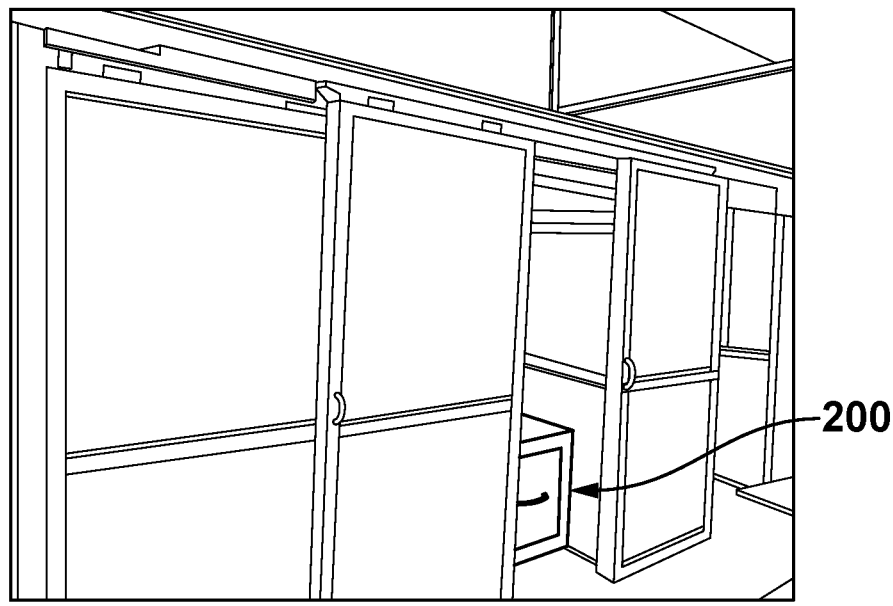
FIGS. 10-11 show the installation of the smart air-purifier between two cabins to handle them at a same time in one embodiment of the present invention.
Figure 11:
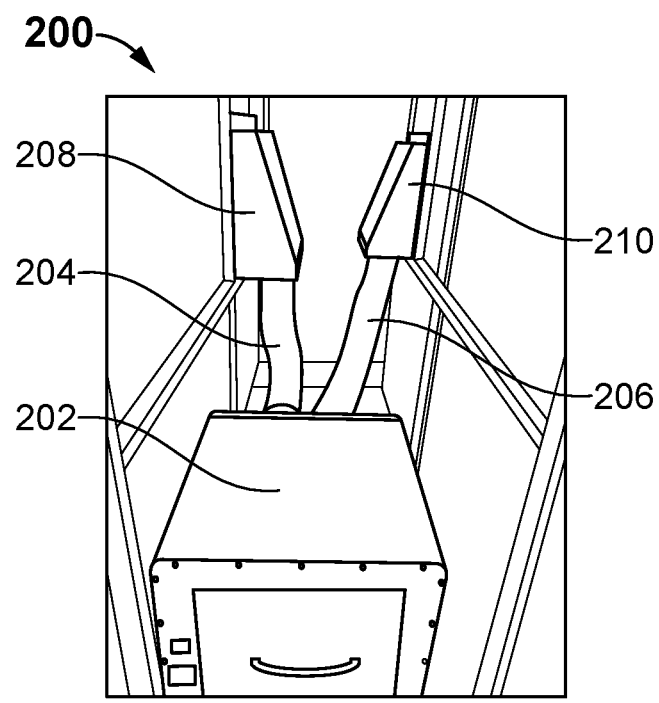
Figure 12:
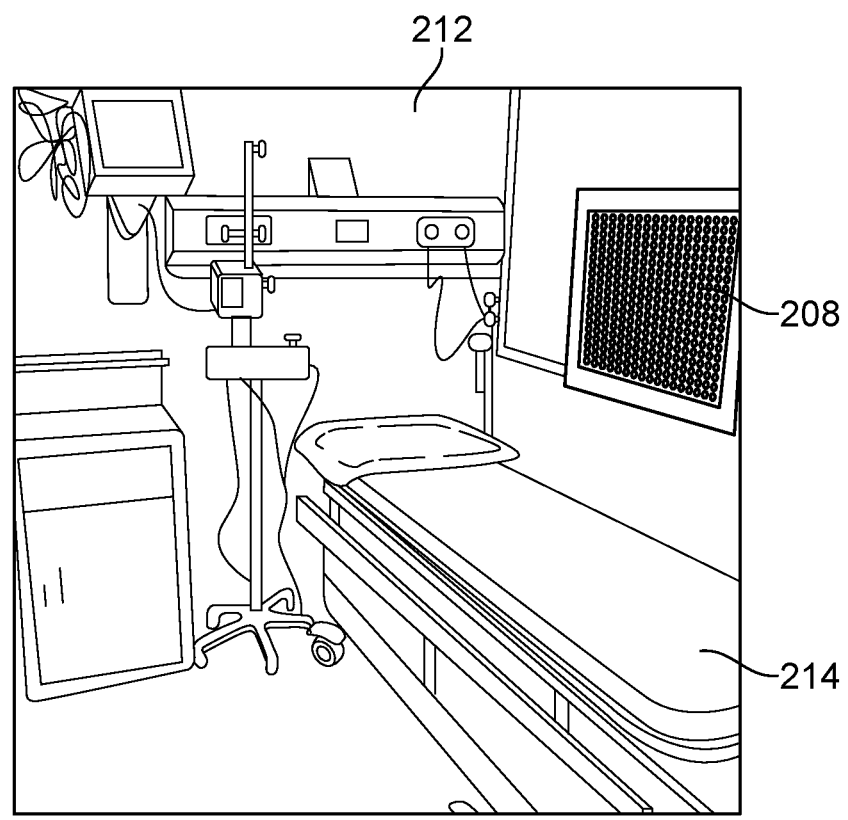
FIG. 12 shows an inside view of the cabin installed with the smart air-purifier in one embodiment of the present invention.

Referring to FIGS. 6-12, various views of cabins installed with the smart air-purifier 200, according to one embodiment of the present invention. In one embodiment, the cabin with purifier 200 includes a machine housing 202, one or more cabin beds (214 and 218) in cabins (212 and 216) (as shown in FIGS. 9-12). In one embodiment, the cabin (212 and 216) has a total length of about 8.15' and 15.02' respectively (as shown in FIGS. 6 and 7). In one embodiment, the length of each cabin (212 and 216) is about 6' to 6.02' respectively. In one embodiment, the system 200 is fixed between the plurality of cabins (212 and 216) that are spaced apart about 3' distance (as shown in FIG. 7). In one embodiment, the cabin bed (214 and 218) has a width of about 3.15' and the remaining space of the cabin (212 and 216) is about 2.70' to 2.87' width. In one embodiment, the cabin (212 and 216) is also designed to about 4' width for the cabin bed (214 and 218) and 3.85' for the remaining space (as shown in FIG. 8).

Figure 13:
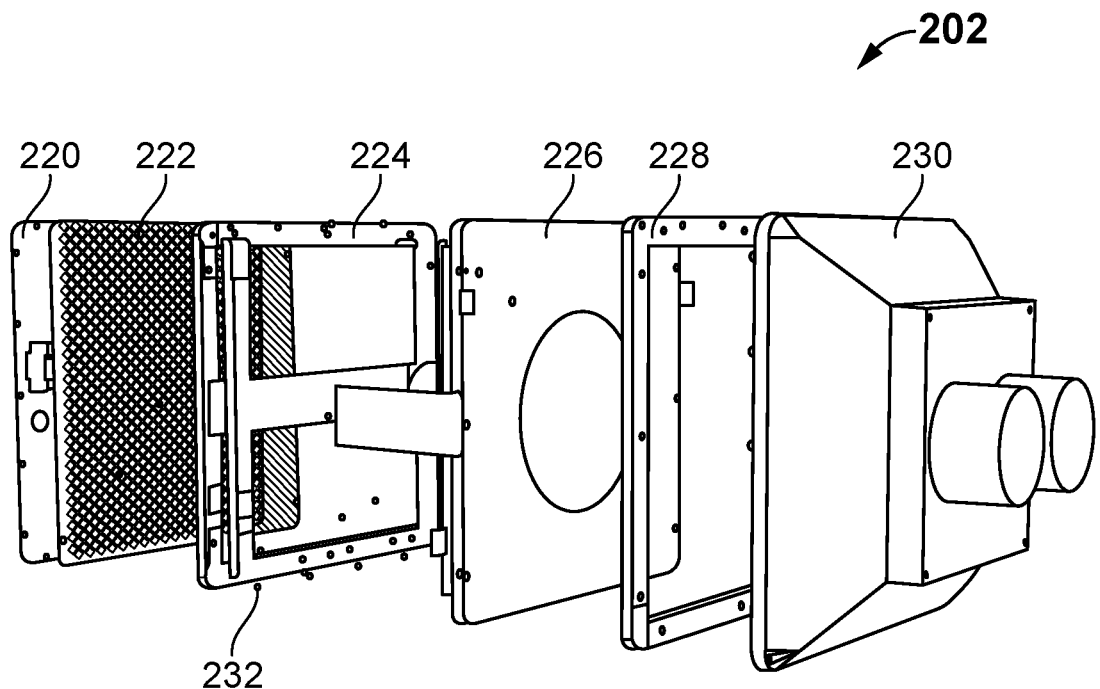
FIG. 13-15 show an exploded view of an air filter in one embodiment of the present invention.
Figure 14:
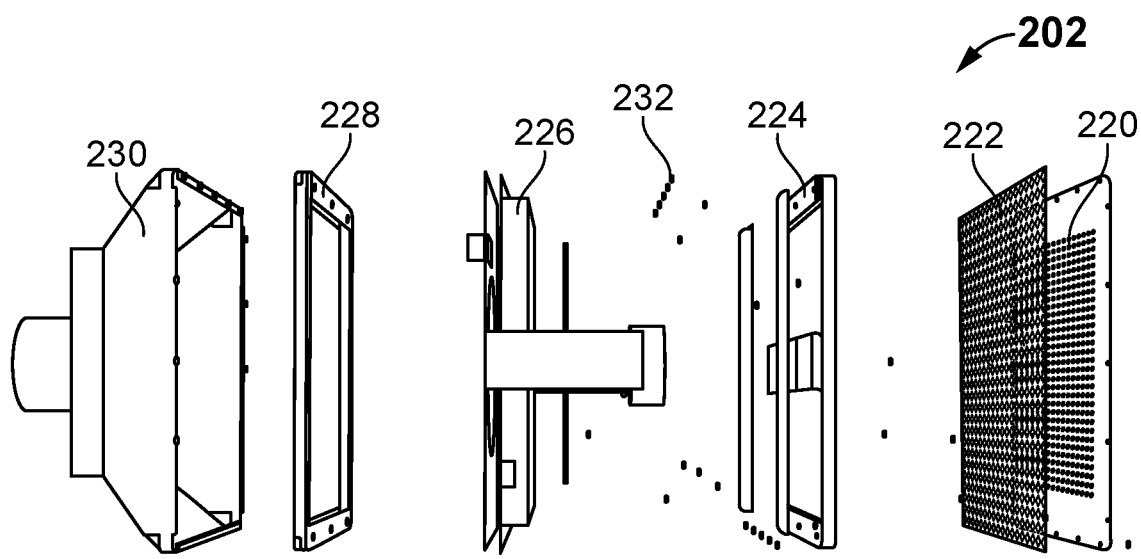
Figure 15:
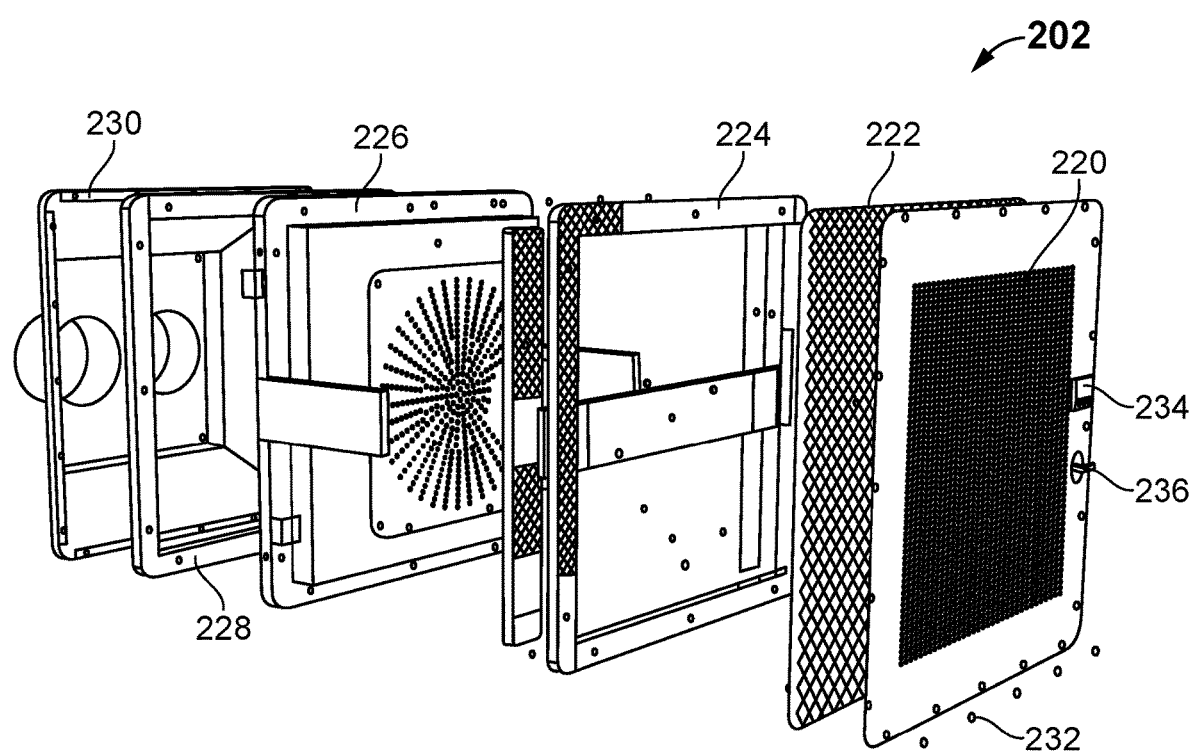

Referring to FIGS. 13-15, an exploded view of the machine housing 202, according to one embodiment of the present invention. In one embodiment, the machine housing 202 comprises a front housing 220 and a back housing 230. In one embodiment, the back housing 230 further includes one or more holes for receiving the air tubes. In one embodiment, the machine housing 202 further includes a filter 222 fixed next to the front housing 220. In one embodiment, the filter 222 is used to circulate the air and capture particles and gases. In one embodiment, the machine housing 202 further includes a front frame 224 attached with the front housing 220 and a back frame 228 attached with the back housing 230. In one embodiment, the machine housing 202 further includes a plurality of fastening holes for receiving fasteners 232. In one embodiment, the back frame 228 further includes an attachment with a slot for receiving a high-efficiency particulate air (HEPA) filter 226. In one embodiment, the machine housing 202 further includes an ON and OFF switch 234 and a button 236 (as shown in FIG. 15).

Referring to FIGS. 16-20, screenshots (300, 400, 500, 600, and 700) of various real-time data for analysis, according to one embodiment of the present invention. In one embodiment, the real-time data from the air purifier is analyzed using IoT to perform surveillance to capture and monitor infection prevention and control data. In one embodiment, the real-time data includes energy consumption, life of the filter, filter replacement alert, room air quality parameters of PM 2.5 and $CO_2$ level. In one embodiment, all the data are uploaded in real-time and are available for download to a system in excel format for further analysis. In one embodiment, the system complies with mandates of the National Accreditation Board for Hospitals & Healthcare Providers (NABH) Clause HIC.6. In one embodiment, the data is displayed in the user device. In one embodiment, the real-time data is accessible through a user device or mobile application via the server.

Figure 16:
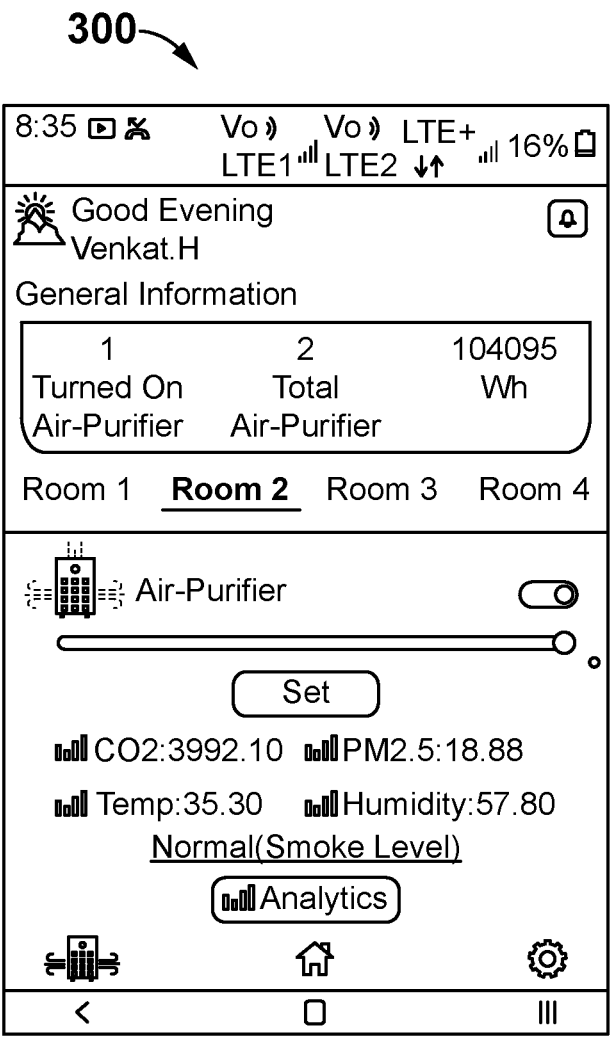
FIGS. 16-20 show a screenshot of various real-time data for analysis in one embodiment of the present invention.
Figure 17:
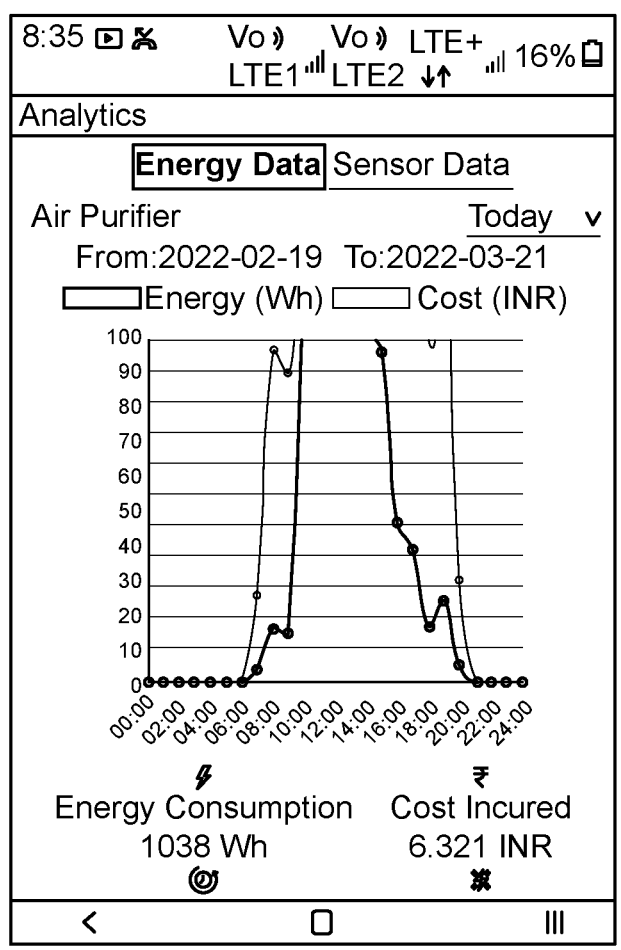
Figure 18:
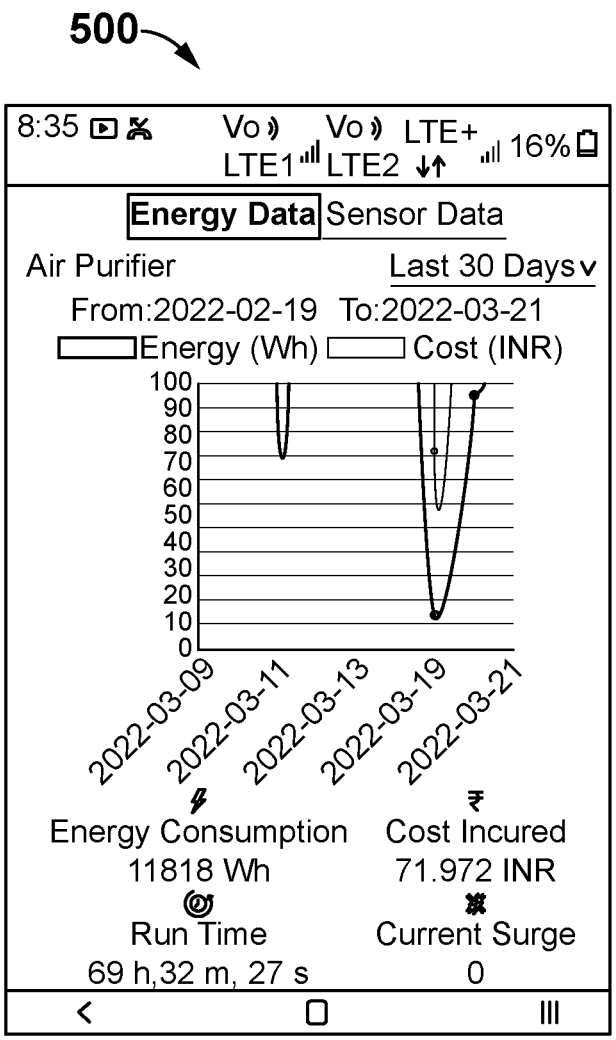
Figure 19:
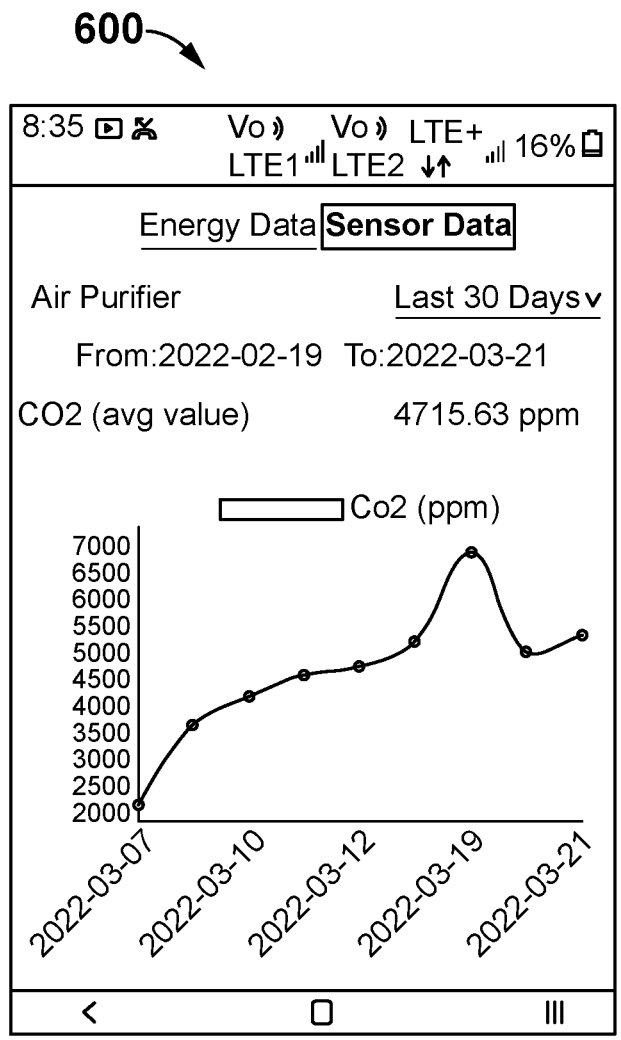
Figure 20:
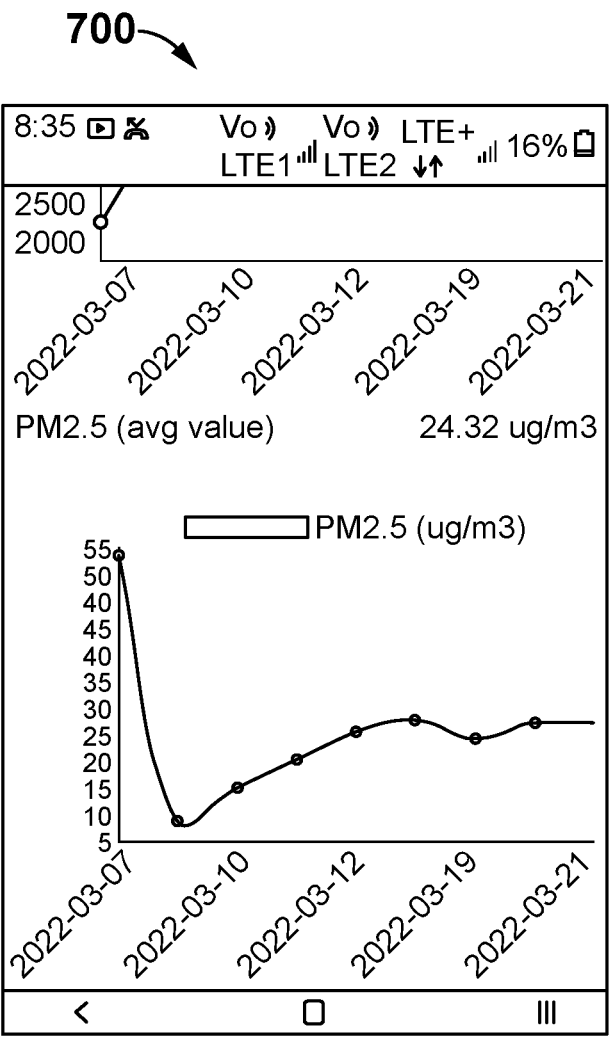

In one embodiment, the screen short 300 displays a user interface displays the air-purifier control data in a dashboard to the customer for analysis anywhere using IoT. In one embodiment, the dashboard includes user name, general information of air-purifier such as number of air-purifiers turned ON, total number of air-purifiers etc. In one embodiment, the dashboard further displays various rooms with respective air-purifiers, humidity level, temperature level etc. (as shown in FIG. 16). In one embodiment, the screen shorts (400 and 500) display an energy data with a graphical representation. It also displays energy consumed, cost incurred, run time, and current surge (as shown in FIGS. 17 and 18). In one embodiment, the screen short 600 also displays a sensor data for the last 30 days with a graphical representation or trend chart (as shown in FIG. 19). In one embodiment, the screen short 700 further displays the PM 2.5 sensor data in the graphical representation or trend chart (as shown in FIG. 20).

Advantageously, the system of the present invention provides a one-stop solution for improved air quality in a negative pressure enclosure in a short time. Further, the negative pressure enclosure doubles up to clean the room air where it is working, and two cabins can be handled by one EAT. The benefits are HEPA Filter are H14+ Grade, lowest power consumption (i.e., 1 unit in 4½ hrs.), CCM Index Grade-P3, 90% Decay in 25 mins and 99.998% Cleaning Efficiency. The system also creates the best sterile environment in enclosed spaces, in the shortest time at affordable costs. Further, the system provides the best AI-ready, smart air purification systems, for contamination control and infection prevention conforming to CDC & WHO norms. Further, the negative pressure enclosure leverages this air purification technology but is customized as a very affordable alternative to the current system of Negative pressure rooms which are very high in CAPEX as well as operating costs. Further, the system of the present invention also protects other people in the room, outside of the NPE from the airborne infectious agents carried by the person inside the NPE.

Preferred embodiments of this invention are described herein, including the best mode known to the inventors for carrying out the invention. It should be understood that the illustrated embodiments are exemplary only and should not be taken as limiting the scope of the invention.

The foregoing description comprise illustrative embodiments of the present invention. Having thus described exemplary embodiments of the present invention, it should be noted by those skilled in the art that the within disclosures are exemplary only, and that various other alternatives, adaptations, and modifications may be made within the scope of the present invention. Merely listing or numbering the steps of a method in a certain order does not constitute any limitation on the order of the steps of that method. Many modifications and other embodiments of the invention will come to mind to one skilled in the art to which this invention pertains having the benefit of the teachings in the foregoing descriptions. Although specific terms may be employed herein, they are used only in generic and descriptive sense and not for purposes of limitation. Accordingly, the present invention is not limited to the specific embodiments illustrated herein.

What is claimed is:
1. A smart air-purification system for providing contamination control and infection prevention installed in a negative pressure enclosure to handle more than one cabin, comprising:
a machine housing that encloses an air filter unit configured to remove airborne particles from air, the machine housing is connected to at least two air-purifiers via one or more air tubes respectively, for cleaning two cabins at a time;

a four-node controller inside the machine housing configured to switch on and off the system;

one or more ultraviolet (UV) lamps and an ionizer enclosed inside the machine housing;

one or more sensors fixed away from the machine housing in a sensor box, configured to monitor the air quality and maintain the air quality up to 10 micrograms per cubic meter;

a server in communication with the air-purifier system via a communication network configured to store a plurality of real-time data of the air-purifier system; and a user device in communication with the server via the communication network configured to access the plurality of data stored in the server, wherein the data is analyzed using the smart air-purification system to perform surveillance to capture and monitor infection prevention and control data.

2. The system of claim 1, is an artificial intelligence (AI) based smart air purification system for providing contamination control and infection prevention.

3. The system of claim 1, wherein the filter unit includes a high efficiency particulate air (HEPA) filter.

4. The system of claim 1, wherein the machine housing further comprises one or more air flow paths that provides an ability to handle more than one cabins at a time.

5. The system of claim 1, wherein the user device is configured to communicate with the server via the communication network using a dedicated application software or mobile application or web-based application, or desktop application.

6. The system of claim 5, wherein the dedicated application software has a dashboard and one or more air purifier controls.

7. The system of claim 6, wherein the dedicated application software with the dashboard and one or more air purifier controls provide data to customers for analysis anywhere.

8. The system of claim 1, wherein the user device is at least any one of a smartphone, a mobile phone, a tablet, a laptop, and a desktop.

9. The system of claim 1, wherein the one or more sensors are a set of PM 2.5 sensors, a $CO_2$ sensor, a humidity sensor, and a temperature sensor.

10. The system of claim 1, further includes a smoke sensor.

11. The system of claim 1, wherein the real-time data includes energy consumption, life of the filter, filter replacement alert, room air quality parameters, and $CO_2$ level.

* * * * *